(12) United States Patent
Sreenivasan et al.

(10) Patent No.: US 11,074,485 B2
(45) Date of Patent: Jul. 27, 2021

(54) SYSTEM AND METHOD FOR IDENTIFYING OPTIMAL EFFECTIVE COMMUNICATION CHANNEL FOR SUBJECT ENGAGEMENT

(71) Applicant: KONINKLIJKE PHILIPS N.V., Eindhoven (NL)

(72) Inventors: Rithesh Sreenivasan, Bangalore (IN); Aart Tijmen Van Halteren, Geldrop (NL); Karthik Srinivasan, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 121 days.

(21) Appl. No.: 16/451,237

(22) Filed: Jun. 25, 2019

(65) Prior Publication Data
US 2020/0012897 A1    Jan. 9, 2020

Related U.S. Application Data

(60) Provisional application No. 62/695,228, filed on Jul. 9, 2018.

(51) Int. Cl.
*G06K 9/62* (2006.01)
*G06N 5/04* (2006.01)
*G06N 20/00* (2019.01)

(52) U.S. Cl.
CPC ......... *G06K 9/6263* (2013.01); *G06K 9/6256* (2013.01); *G06N 5/04* (2013.01); *G06N 20/00* (2019.01)

(58) Field of Classification Search
CPC .... G06K 9/6263; G06K 9/6256; G06K 9/627; G06K 9/00335; G06N 5/04; G06N 20/00; G16H 50/50; G16H 80/00

USPC .......................................................... 382/159
See application file for complete search history.

(56) References Cited

U.S. PATENT DOCUMENTS

| | | | |
|---|---|---|---|
| 2003/0144580 A1* | 7/2003 | Iliff ....................... | G16H 15/00 600/300 |
| 2005/0065813 A1* | 3/2005 | Mishelevich .......... | G16H 50/30 705/2 |
| 2005/0108052 A1* | 5/2005 | Omaboe ................ | G06Q 50/22 705/2 |
| 2005/0182743 A1* | 8/2005 | Koenig .................. | G06Q 99/00 |

(Continued)

FOREIGN PATENT DOCUMENTS

WO    2008030850 A1    3/2008

OTHER PUBLICATIONS

More About You! Survey, https://acc.moreaboutyou.philips.com/demo/may_en_20_30, 2019.

(Continued)

*Primary Examiner* — Juan A Torres

(57) ABSTRACT

A machine learning based recommendation model, including a supervised learning classifier configured to receive input training data that includes a plurality of behavioral determinants, a supervised learning model configured to receive subject input data that includes a plurality of behavior determinants, wherein the supervised learning model outputs a predicted behavior of a subject, and a channel selection module configured to receive the subject input data and the predicted behavior and to determine a recommended communication channel for the subject to follow to achieve the predicted behavior.

12 Claims, 5 Drawing Sheets

(56) References Cited

U.S. PATENT DOCUMENTS

2005/0288965 A1* 12/2005 Van Eaton ............. G06Q 50/22
 705/2
2013/0191319 A1* 7/2013 Biehl ....................... G06N 5/04
 706/52
2016/0232805 A1 8/2016 Gibson et al.

OTHER PUBLICATIONS

Patient Health Questionnaire, https://acc.moreaboutyou.philips.com/user_surveys/u5ppxy9zeupmmazazzfy/sections/1264, 2019.
Kish, L. et al., "Patient Engagement is a Strategy, Not a Tool", HL7 Heath Standards, 2014.
"Text Messaging for Patient Engagement: The Key to Unlocking Positive Healthcare Outcomes", Upland Mobile Messaging, https://uplandsoftware.com/mobile-messaging/resources/ebook/text-messaging-for-patient-engagement-the-key-to-unlocking-positive-healthcare-outcomes/, 2019.

\* cited by examiner

SYSTEM AND METHOD FOR IDENTIFYING OPTIMAL EFFECTIVE COMMUNICATION CHANNEL FOR SUBJECT ENGAGEMENT

CROSS-REFERENCE TO PRIOR APPLICATIONS

This application claims the benefit of U.S. Patent Application No. 62/695,228, filed on 9 Jul. 2018. This application is hereby incorporated by reference herein.

TECHNICAL FIELD

Various embodiments relate to communication systems and more particularly communication channels used in telehealth or clinical settings.

BACKGROUND

There are many communications options possible between an entity and a subject. In a telehealth/clinical setting subjects can be engaged using various communication channels such as text messaging, e-mail, communication via tablet or computer systems, telephone calls, letters, smartphones, etc. The way a subject engages with these technologies depends on their personal communication preferences, comfort with technology, and other personal determinants.

SUMMARY

Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Embodiments include a machine learning based recommendation model, including a supervised learning classifier configured to receive input training data that includes a plurality of behavioral determinants, a supervised learning model configured to receive subject input data that includes a plurality of behavior determinants, wherein the supervised learning model outputs a predicted behavior of a subject, and a channel selection module configured to receive the subject input data and the predicted behavior and to determine a recommended communication channel for the subject to follow to achieve the predicted behavior.

The selected channel, predicted behavior, and actual behavior of the subject may be used to further train the supervised learning model. The supervised learning model may be trained using testing input data.

The channel selection module may be trained using the training input data. The channel selection module may use heuristic rules.

The channel selection module may produce a table of recommended channels associated various subject input parameters.

The channel selection module may be configured to overrule the recommended channel based upon a severity of a subject disease burden.

Embodiments also include a method of producing machine learning based communication channel recommendation model, including training a supervised learning classifier using input training data that includes a plurality of behavioral determinants, training a supervised learning model configured using test input data that includes a plurality of behavior determinants, wherein the supervised learning model outputs a predicted behavior of a subject, and training a channel selection module based upon the test input data and the predicted behavior, wherein the channel selection module is configured to determine a recommended communication channel for the subject to follow to achieve the predicted behavior.

BRIEF DESCRIPTION OF THE DRAWINGS

Additional objects and features of the invention will be more readily apparent from the following detailed description and appended claims when taken in conjunction with the drawings. Although several embodiments are illustrated and described, like reference numerals identify like parts in each of the figures, in which:

DETAILED DESCRIPTION

Figure 1:
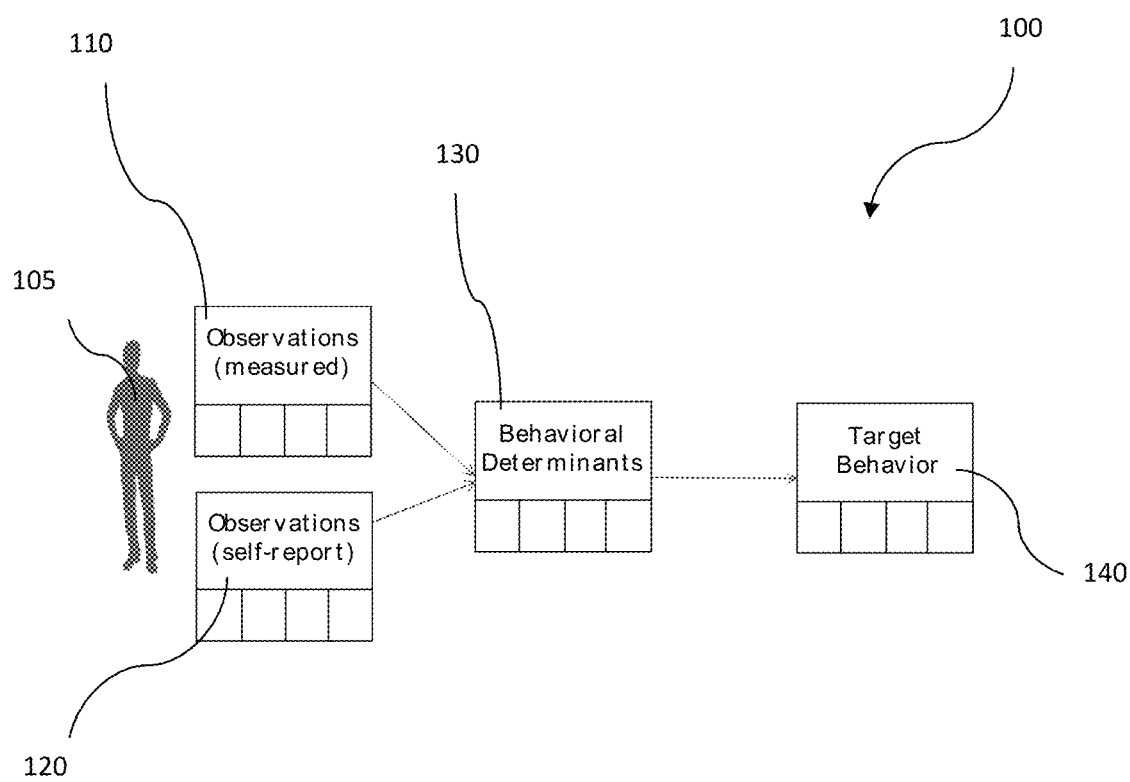
FIG. 1 illustrates a health behavior profile in accordance with embodiments described herein.

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or illustrated herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments. Descriptors such as "first," "second," "third," etc., are not meant to limit the order of elements discussed, are used to distinguish one element from the next, and are generally interchangeable. Values such as maximum or minimum may be predetermined and set to different values based on the application. When steps of manufacture, process of using, or other method steps are described or claimed, the order of steps given is not constrained by the order presented, and may vary. Terms such as "below," "above," "right," and "left," may be used for relative orientation of a device or apparatus as illustrated in a figure. If an apparatus or component of a figure may be rotated and still function in a similar manner to what is described, the directional terms are not limited to the orientation illustrated in a particular figure. "Below" when rotated may become "right," or "left" or "above." The same holds true for the other directional indicators.

Optimal subject engagement may include a profile to be built so that the subject may be contacted and engaged through an optimal communication channel to receive content. The content in the optimal communication channel will direct the subject to interact with the entity in a manner designed to achieve a desired goal of the entity. In the telehealth establishment, there is a challenge to engage patients. Because the engagement is remote, doctor-patient interactions are performed from a distance, and communication is limited. As a result it is important to reach patients so that further care may be provided.

Care managers have a responsibility to identify gaps in the caring of individuals within a population. Population health management tools may help care managers identify which subjects are in need of additional care and support.

Embodiments described herein may be involved in managing large groups of subjects with a purpose of manipulating patient behavior to achieve a desired outcome. The communication system may take into account patient communication preferences as a factor in order to achieve the desired outcome.

For care managers that manage the health of an entire population, implementing outreach programs over the correct channels may enhance the effectiveness of their programs. For example, rolling out a health screening program targeted towards a specific subject population may involve preparing outreach content (e.g., an invitation to enroll in a health screening program), selecting the target population (i.e., finding those eligible for the screening), personalizing the content to individual subjects, selecting the communication channels over which the outreach will be delivered to improve the likelihood that those targeted will engage, enabling subjects to reach the provider over different channels to complete the enrolment process, and following up to ensure that enrolled subjects actually attend and complete the screening.

In present implementations, providers may use a single (or dual—one primary and one backup) channel to deliver information to the subjects. Neither the context (of the outreach), the psycho-social determinants of the subject, nor the subject's familiarity/comfort/effectiveness of past interactions over the specific channel are considered. This leads to a very low uptake of such outreach programs and in many cases, the providers need to resort to multiple interventions (e.g., calling subjects directly) over an extended period of time to make the screening program effective. Such repeat interactions are time consuming for the care manager.

Another scenario where the subject's psycho-social profile and interaction context becomes important is when a subject is enrolled into a specific care program. Adherence is key to the success of the program. Subjects may potentially be offered multiple means by which they may complete and share the results of their daily tasks (vitals, activities, assessments). Successful adherence to the care plan depends on a subject's social determinants of health (SDoH), comfort with technology/channels as well as the care context. Embodiments described herein determine the correct channels and interaction models as well as adapt to these channels and models dynamically based on a subject's behavior over time. This leads to a more effective population health management model.

Embodiments described herein include a computer-implemented method for learning the appropriate communication channel for subject engagement based on a behavior profile of subjects and retrospective machine learning of subject interactions with various communication channels. The behavior profile may include a physical and/or mental health behavior profile.

Embodiments describe methods to influence the behavior of a subject to take a course of action. The message may be individualized. Embodiments describe what type of communication channel a patient will respond to, and what message the communication system is attempting to communicate.

A communication system will be described herein to achieve these and other goals. According to embodiments, types of data may be translated into what are known as behavioral determinants. Through machine learning the communication system may be trained to view a subject's behavioral determinants and determine an optimal communication channel for communication success.

According to embodiments, once a communication is started in a communication channel, interaction may switch to another channel. This may be known as omni-channel implementation. Omni-channel implementation may ensure communication is continued between an office and a subject even after the communication changes channels. The communication may continue and be maintained using another mode. There is no limit or restriction regarding what communication mode may follow another. For example, a communication from a communication system to a subject may start with a letter. If the subject does not respond in a timely fashion, communication may switch to a phone call, e-mail, or text message. When the subject arrives for an office visit, such as the doctor's visit, the patient may be polled to determine the most effective communication that caused the subject to respond, which is then fed back into the communication system.

In one scenario in telehealth, a subject may be identified with a specific target behavior. For example, a patient may be called into a doctor's office. The target behavior is going to the doctor's office. Embodiments may use various methods to determine an optimal communication path with the patient to have them appear at the desired location. Embodiments may objectively identify an appropriate channel and format for involving the subject in the care delivered. Embodiments will improve subject engagement by feeding back into the communication system a success or failure of the outreach efforts, and then further optimize for future subject-provider interactions.

Embodiments include a computer-implemented method for determining the optimal channel and format for engaging a subject, given the individualized psycho-social determinants of that subject. The communication system includes at least three modules including a platform for omni-channel subject engagement delivery, a module to extract subject determinants of health, and a machine learning model to combine subject interactions and determinants of health.

FIG. 1 illustrates a health behavior profile 100 according to embodiments described herein. The health behavior profile 100 links together the observations from one or more subjects 105. Observations include both measured observations 110 and self-reported observations 120. The measured observations 110 and self-reported observations 120 may be translated into behavioral determinants 130 (a.k.a. psycho-social determinants) of the subject(s) 105 and target behavior 140 thereof. The target behavior 140 is the desired behavior that the communication system aims the subject to achieve.

Measured observations 110 include a first type of data such as clinical data collected by medical practitioners in a medical setting. They may be measurements like blood pressure, weight, cholesterol, blood sugar levels, heart-rate and temperature. These observations are collected using medical devices at home or business, at a clinic or other medical establishment. Self-reported observations 120 may be collected by surveys, survey questions, and the like. Various surveys like MAY (More about you) and PHQ9 survey (which measures depression) may be used for eliciting responses from the subject. Both types of observations are compiled as data of a patient.

Figure 2:
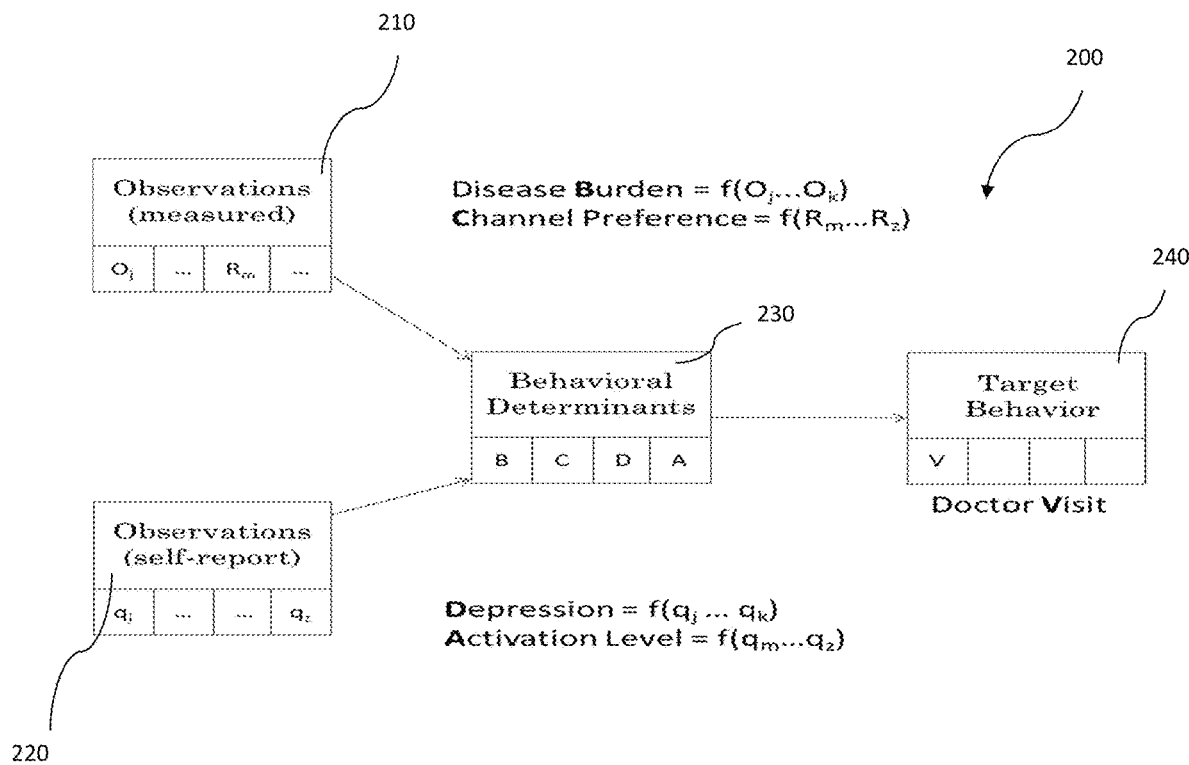
FIG. 2 illustrates an example behavioral profiling of care giver visits or coaching in accordance with embodiments described herein.

FIG. 2 illustrates an example health behavioral profile 200 of desired outcomes in accordance with embodiments described herein. Self-reported observations 220 may include questions answered by a subject. For example, for the topic of depression (D), each answer to a question may indicate a depression level that is a behavioral determination for depression. A second self-reported observation could be activation level, which may be dubbed Activation (A). The answers lead to the D and the A in a behavioral determinants 230 vector. Observations include health status as measured by various devices. The health behavioral profile 200 includes a disease burden function of the device readings to calculate a subject's disease burden (B), another behavioral determinant.

Another behavioral determinant 230 is a subject's preference for a communication channel. This preference may be determined by the self-reported observations 220, or by repeated observation of a subject by a caregiver. Preferred communication channel may be designated "C." While a subject may think they know the best communication channel to reach them, embodiments described herein use the behavioral determinants 230 to determine the actual optimal communication channel that will influence the subject to perform a target behavior 240.

Embodiments are not limited to four determinants, but are illustrated and discussed as such by way of example. Behavioral determinants may range in the dozens, including but not limited to coping style, self-efficacy and health engagement. As illustrated in FIG. 2, all four determinants may be assembled into a BCDA vector. The BCDA vector is used to determine how the behavioral determinants influence the target behavior 240, such as people's doctor visit behavior.

After the communication system receives all the measured observations 210 and self-reported observations 220 and determines behavioral determinants 230, the communication system uses these values to determine an optimal communication method to influence the subject to perform the target behavior 240.

Embodiments described herein describe a communication system that will reach out to a patient in a manner that will cause the patient to most likely respond and take a desired action. If a subject has a preferred mode of communication, this preference is stored as channel preference "C," then balanced with the other factors. Considering other behavior determinants A, B, and D, the communication system may recommend a different communication channel than is selected by an individual patient. The different behavior determinants A, B, C, and D are data that receive different weights in a machine learning algorithm when determining an optimal communication outreach strategy for a patient.

As one illustration, the behavioral determinants 230 may include four different factors. A function of a subset of measured observations 210 may be used to compute a disease burden (B). A function of a subset of self-reported observations 220 may be used to compute depression levels (D). A function of another subset of self-reported observations 220 may be used to compute activation levels (A). A function of another subset of self-reported observations of a subject's indicated preferences for various channels may be used to compute channel preference (C). The channel preference is one factor in the set of behavior determinants A, B, C, and D. The module that computes the behavioral determinants 230 performs calculations to arrive at the values for B, C, D, and A. Based on these values, an optimum communication mode will be determined to influence the subject to perform the target behavior desired to place the subject in proper contact with the desired entity, or to take the desired course of action. The target behavior 240 may represent an end goal of a care giver visit (V) or coaching (C), among other desired outcomes.

One behavioral determinant factor may consider the mental health state of a patient, and may be labeled Depression having the designation, "D." Data may be accumulated for this factor by asking the subject to fill out a questionnaire revealing a state of their mental health via a group of questions. Variables $q_j$ through $q_z$ may be based on answers to questions such as, "how do you feel?" or "are you happy or sad?" A patient may answer the questions, then the communication system compares their answers to answers stored in memory, to determine an appropriate depression level D for that subject.

Figure 3:
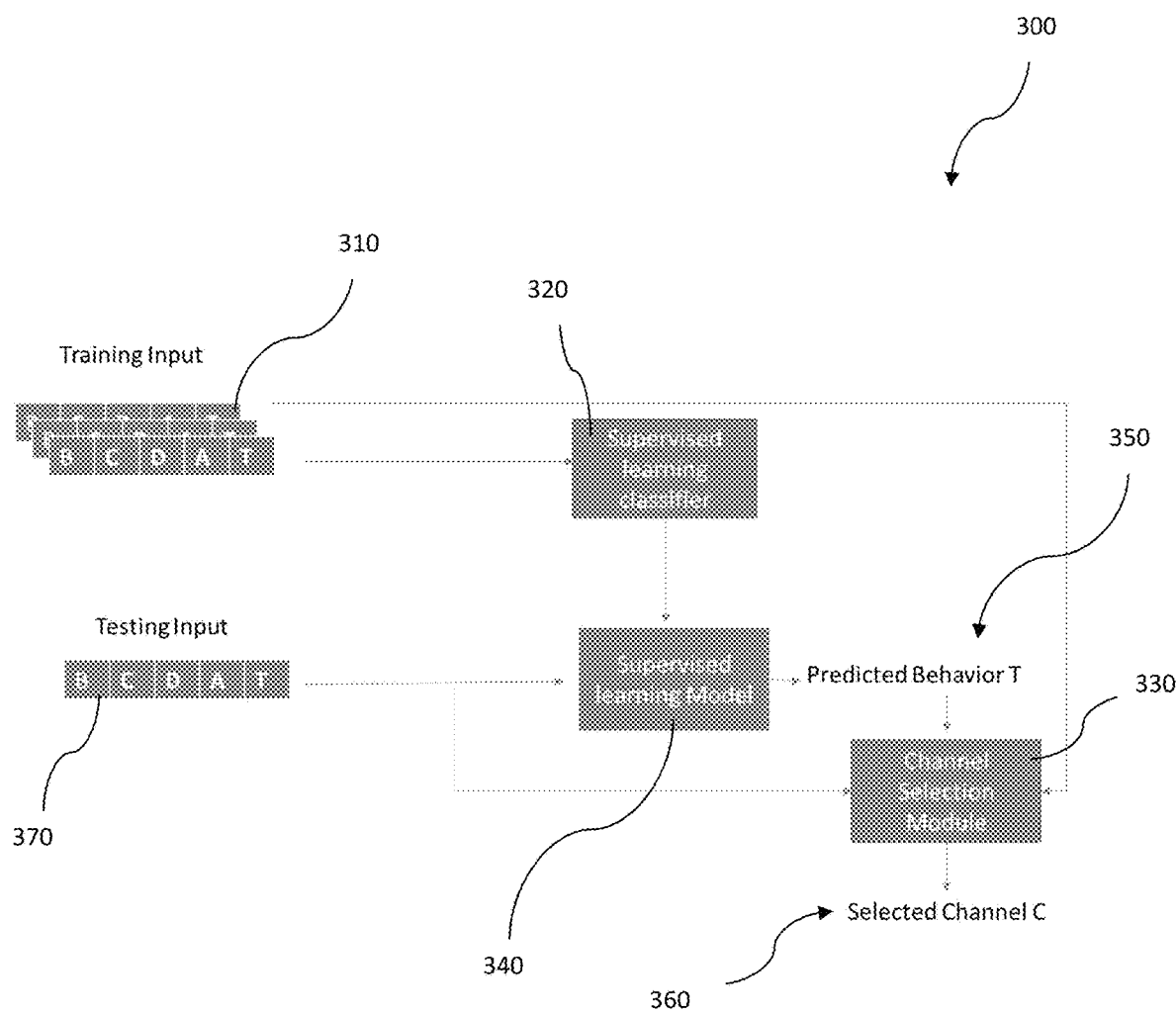
FIG. 3 illustrates a machine learning based recommendation model and channel selection module in accordance with embodiments described herein.

FIG. 3 illustrates a machine learning based recommendation model 300 and channel selection module 330 in accordance with embodiments described herein. The machine learning based recommendation model 300 takes as training input 310 the tuple (B, C, D, A) representing the behavioral determinants 230 and the target behavior 240 T(V/C/ . . . ). Based on retrospective data there are multiple records of such tuples. A supervised machine learning classifier 320 (support vector machine, decision tree, neural network) is then trained on these tuples with a cost function being accuracy of target behavior prediction. A channel selection module 330 may learn the relationships between behavioral determinants 230 model variables (B, D, A) and the channel preferences (C). The channel selection module 330 then selects a selected channel 360 based on the behavior profile and predicted behavior 350 from a previous model. The channel selection module 330 can also be tuned using heuristic rules observed from retrospective (population level) data. Based on the effectiveness of an interaction on a specific (recommended) channel on new data, the channel selection module 330 can be further tuned. The channel selection module 330 can also overrule the recommended channel based on severity of disease burden (B) (for example, when the severity of the message is of a nature that it determines a phone call).

Referring to FIG. 2, the vector can be inserted into the machine learning based recommendation model 300 which can output, using the combination of behavioral determinants 230, a suggested communication channel to arrive at the target behavior 240. Determination of behavioral determinants 230 and the target behavior 240 is offline learning that will be put into a supervised learning model 340 that will be used to predict how a subject 105 will perform based given a BCDA vector. Given these inputs, the machine learning based recommendation model 300 selects the appropriate communication channel having a highest likelihood of success.

The machine learning based recommendation model 300 may be a form of reinforcement learning that evolves over time with feedback based on a success of the selected communication channel. The machine learning based recommendation model 300 may be a platform for omni-channel subject engagement.

As illustrated in FIG. 3, the predicted behavior 350 is the behavior the communication system desires in response to a subject's situation. The predicted behavior 350 is the target behavior 240 a doctor or other entity would like a subject to perform such as visiting a doctor's office, getting a medical screening, doing a phone consultation, getting additional testing, or the like. Embodiments put into motion, to persuade a subject, what's the most likely or successful way of doing that.

Embodiments do not include communication from subject to doctor. If a subject wants to communicate through a text message or communication method of their choice, they have the option to do so.

The communication system tracks the successes of communications attempts and changes over time. Based on a prediction made by the communication system, a determination is made whether the prediction leads to the desired effect. The prediction is observed, then gets fed back into the training input 310 "C" as illustrated in FIG. 3. Different communication channels and models may be tailored subject to subject.

To determine a supervised learning model 340, an initial supervised machine learning classifier 320 is performed based on an entire population. Once the supervised learning model 340 is stored, and the communication system learns and observes responses of the subject 105, that information is used by the channel selection module 330 to derive the selected channel 360. This is an example of online learning.

Embodiments may find the selected channel 360 based on a plurality of observed, self-reported, and fed back data. A method may start with a channel preference of the patient, which is based on initial settings. As the communication system develops over time, the channel preference of the patient changes, depending on how the patient responds to a previous interaction.

The machine learning based recommendation model 300 includes two models, training and testing. Testing input 370 may include data that includes subsequent testing after the model is complete, or the testing input 370 may include the real input to determine a real outcome. The machine learning based recommendation model may be trained on the historical data it has, as a bootstrap. Once that training is in place the machine learning based recommendation model 300 starts to learn what is a more personalized preference. The machine learning based recommendation model 300 may develop a different supervised learning model 340 for each person.

Figure 4:
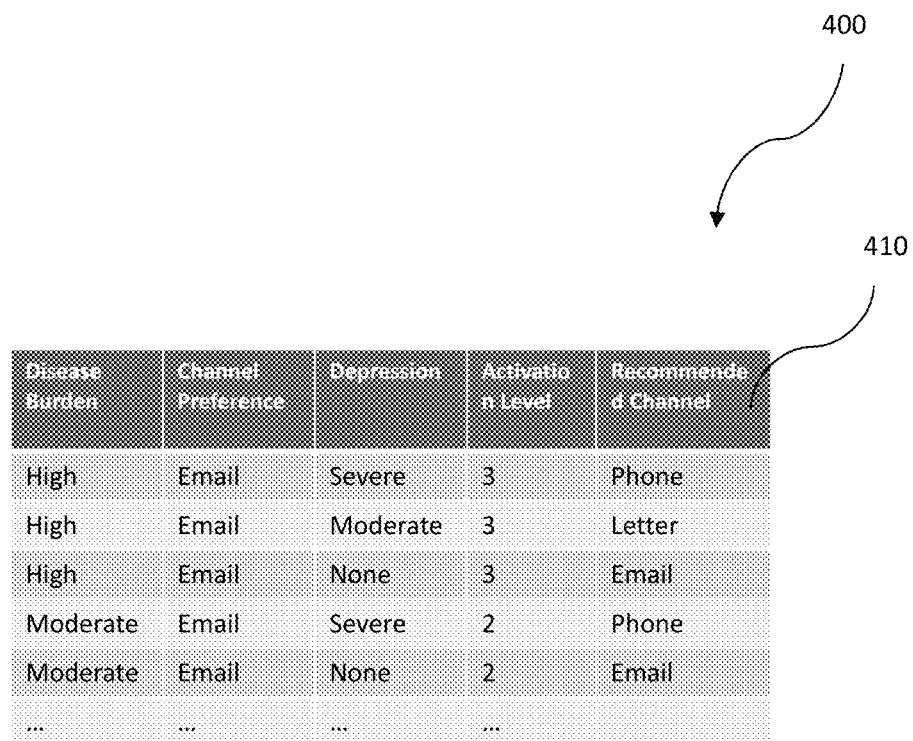
FIG. 4 illustrates an example decision table for recommending a channel in accordance with embodiments described herein.

FIG. 4 illustrates an example decision table 400 for recommending a channel in accordance with embodiments described herein. The decision table 400 could be presented to a clinic, or care manager, or produce a recommended output. Column 410 represents a recommended channel based on the behavioral determinants D, C, B, and A.

Referring to FIG. 4, once a determination has been made using the behavioral determinants 230, the communication system may communicate its recommendations to a subject 105 in various ways. A recommended channel may include communication by phone, letter, or e-mail. Though not listed, one recommended channel 410 may include smart speakers that are in a vicinity of a subject. A messaging system such as What'sApp®, Facebook Messenger®, Outlook®, or similar may be used to send the message, based on a subject's known communication or social media tendencies. Virtual reality in the form of smart glasses, heads-up displays, or other augmented reality may communicate a message to a subject. Messages may be also on static items such as a pillbox distributed by a caregiver.

Figure 5:
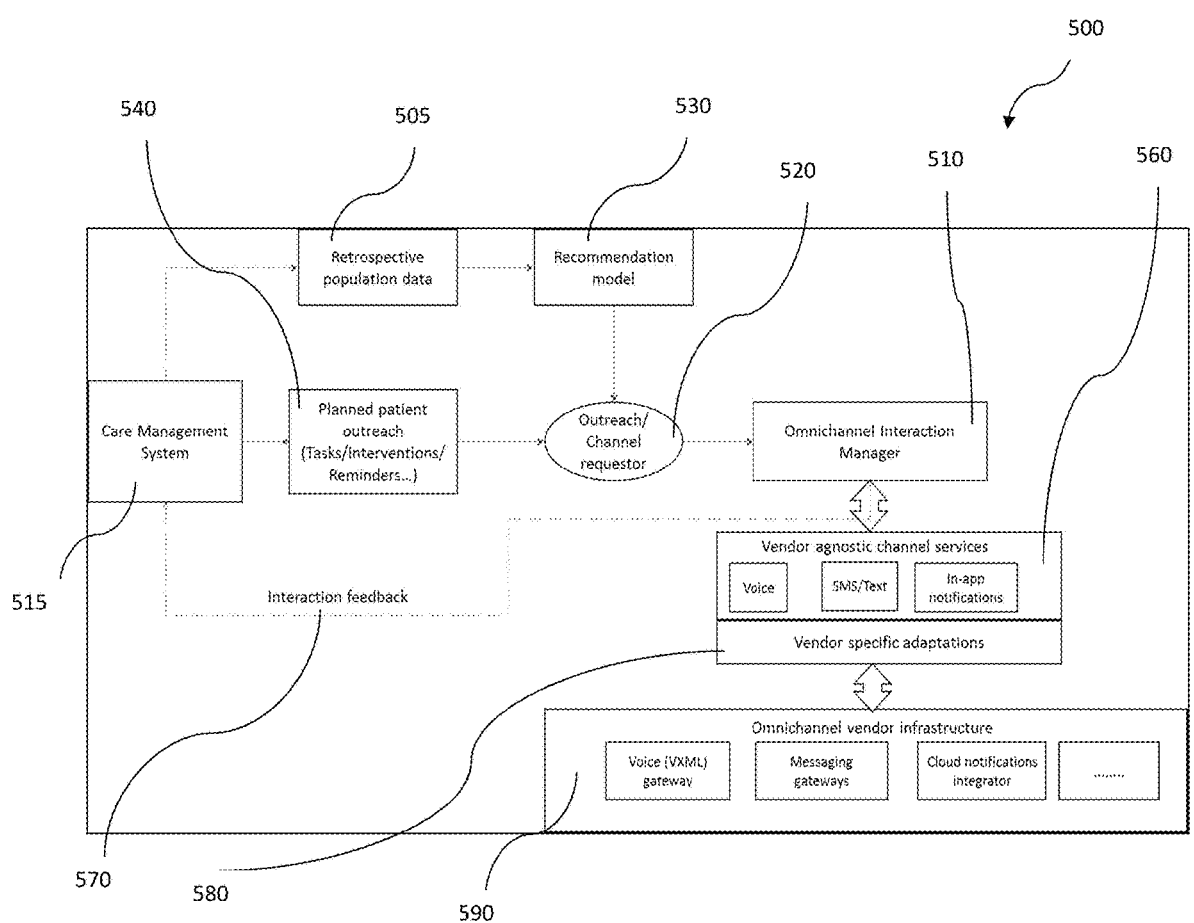
FIG. 5 illustrates an end to end platform for omni-channel subject engagement in accordance with embodiments described herein.

FIG. 5 provides a schematic of an end-to-end platform 500 that encompasses components described herein. FIG. 5 illustrates how the recommendation model 530 fits into an overall communication system.

A care management module described herein is responsible for enabling clinical decisions associated with subject care. These include setting up appropriate care protocols for subjects, processing incoming observations and deciding on appropriate outreaches. Outreaches may take various forms including observed and self-reported tasks such as (e.g., take a measurement, respond to a survey), reminders, messages, delivering educational content (e.g., coaching) etc.

Retrospective population data 505 may be used to train the recommendation model 530. An omnichannel interaction manager 510 may determine what channel a subject responds to and send that information back to a care management system 515.

This information is fed into planned patient outreach module 540. The planned patient outreach module 540 may include tasks, interventions, etc. received from the care management system 515.

To maximize effectiveness of outreach, a method may select the correct channel for delivering a message to a subject. The recommendation model 530 may be trained and optimized based on retrospective population data 505 and responsible for emitting the preferred or recommended channel for a specific outreach to an outreach/channel requestor 520.

The outreach/channel requestor 520 combines the outreach request from the planned patient outreach module 540 with the corresponding channel recommendation from the recommendation model 530.

An outreach may be considered as a collection of interactions to be delivered on one or more channels. The end-to-end platform 500 is responsible for managing this delivery across potentially multiple channels. It may include an omnichannel interaction manager 510 responsible for adapting incoming interaction requests and orchestrating their delivery across one or more channels.

A vendor agnostic channel services layer 560 may provide a standardized set of interfaces to deliver channel specific interactions (e.g., sending a message, making a phone call with or without an associated IVR application etc.). Observations such as interactive feedback 570 may be sent back as a channel preference illustrated in FIG. 2, as a behavioral determinant.

Vendor specific adaptations 580 may optimize delivery of interactions over the selected channel and configured vendor. These vendor specific adaptations 580 are responsible for interfacing with corresponding vendor infrastructure 590 to deliver an omni-channel engagement.

The omni-channel services end-to-end platform 500 also provides the ability to monitor and report back the effectiveness of a specific interaction. This feedback can potentially be added to the retrospective population data set to further refine the recommendation model 530.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

The invention claimed is:

1. A communication system configured to implement a machine learning based recommendation model, the communication system comprising:
    a supervised learning classifier configured to receive input training data that includes a plurality of behavioral determinants;
    a supervised learning model configured to receive subject input data that includes the plurality of behavior determinants, wherein the supervised learning model outputs a predicted behavior of a subject; and
    a channel selection module configured to receive the subject input data and the predicted behavior of the subject and to determine a recommended communication channel for the subject as a selected communication channel to follow to achieve the predicted behavior.

2. The communication system of claim 1, wherein the selected communication channel, the predicted behavior of the subject, and actual behavior of the subject are used to further train the supervised learning model.

3. The communication system of claim 1, wherein the supervised learning model is trained using testing input data.

4. The communication system of claim 1, wherein the channel selection module is trained using the training input data.

5. The communication system of claim 1, wherein the channel selection module produces a table of recommended channels and associated various subject input parameters.

6. The communication system of claim 1, wherein the channel selection module is configured to overrule the recommended channel based upon a severity of a subject disease burden.

7. The communication system of claim 1, wherein the channel selection module is configured to overrule the recommended channel based upon a severity of a subject disease burden.

8. The communication system of claim 4, wherein the channel selection module uses heuristic rules.

9. A method of producing a machine learning based communication channel recommendation model, comprising:
    training a supervised learning classifier using input training data that includes a plurality of behavioral determinants;
    training a supervised learning model configured using test input data that includes the plurality of behavior determinants, wherein the supervised learning model outputs a predicted behavior of a subject; and
    training a channel selection module based upon the test input data and the predicted behavior of the subject, wherein the channel selection module is configured to determine a recommended communication channel for the subject to follow as a selected communication channel to achieve the predicted behavior.

10. The method of claim 9, wherein the selected communication channel, the predicted behavior of the subject, and actual behavior of the subject are used to further train the supervisor learning model.

11. The method of claim 9, wherein the channel selection module uses heuristic rules.

12. The method of claim 9, wherein the channel selection module produces a table of recommended channels and associated various subject input parameters.

\* \* \* \* \*